(12) United States Patent
Jespersen

(10) Patent No.: US 6,752,822 B2
(45) Date of Patent: Jun. 22, 2004

(54) BODY TISSUE RETRIEVEL BAG ARRANGEMENT

(76) Inventor: Chris A. Jespersen, 1086 King Rd. Apt. Ju 115, Malvern, PA (US) 19355-1975

( * ) Notice: Subject to any disclaimer, the term of this patent is extended or adjusted under 35 U.S.C. 154(b) by 257 days.

(21) Appl. No.: 10/052,884

(22) Filed: Jan. 23, 2002

(65) Prior Publication Data

US 2003/0139767 A1 Jul. 24, 2003

(51) Int. Cl.[7] .............................................. A61B 17/28
(52) U.S. Cl. ...................................... 606/205; 606/114
(58) Field of Search ................................ 606/205–210, 606/113, 114, 127

(56) References Cited

U.S. PATENT DOCUMENTS 5,217,468 A  *  6/1993  Clement ..................... 606/205
6,264,663 B1 *  7/2001  Cano .......................... 606/114
6,383,195 B1 *  5/2002  Richard ...................... 606/114

* cited by examiner

Primary Examiner—Kevin T. Truong
(74) Attorney, Agent, or Firm—Don Halgren

(57) ABSTRACT

A tissue retrieval arrangement for enclosably retrieving body tissue from a mammalian body cavity. The retrieval arrangement comprises an elongated thin walled sheath-like retrieval bag having a proximal end and a distal end. A plurality of receiving tips are arranged on the distal end of the sheath to permit receipt of a grasper jaw in each of the receiving tips and thus permit safe retrieval of a body tissue between the receiving tips when moved by the grasper jaws. The bag is everted over the severed tissue once the receiving tips have grasped the tissue, and the now enclosed tissue and bag may be safely removed from the patient.

7 Claims, 4 Drawing Sheets

BODY TISSUE RETRIEVEL BAG ARRANGEMENT

BACKGROUND OF THE INVENTION

1. Field of the Invention

This invention relates to devices and methods for retrieving mammalian tissue from a body cavity during a laparoscopic procedure.

2. Prior Art

Tissue recovery during a surgical procedure is an important task. This is so because tissue which has been excised should quickly be removed to prevent contamination of the body site by that tissue. Tissue retrieval during a laparoscopic procedure is typically fairly difficult. A laparoscopic procedure is done by pressurizing the peritoneum with a gas such as carbon dioxide, so as to expand the peritoneal cavity, to permit surgical access to the internal body organs. Surgical tools, such as a light source, camera and a trocar, which is a mechanical sleeve that is placed through a slit in the abdominal wall, are inserted into the body cavity so as to provide a video image of the internal organs within the body. Once a portion of the body tissue has been excised, it needs to be removed from within the peritoneal cavity. This excised tissue may contain loose objects which may be spilled into the peritoneal cavity, such objects could be gallstones from the gallbladder, or spilled liquids such as bile from the gallbladder or pus from the inflamed appendix which may contaminate the site to cause medical problems later on for the patient. Access to the surgical site is done through small surgical openings which restrict movement of those surgical tools. Removal of that excised tissue is sometimes awkward or impossible as the tissue is often difficult to grasp, collect and extract due to this limited tool movement and limited tool capabilities.

The prior art contains attempts to capture such tissue in a bag or a sack, for example a "Lapsac" and an "Endobag". Latex condoms have also been tried. Such devices are introduced into the surgical site through a trocar either by a surgical tool or by a specially designed introducer. However, once a prior art bag is in the closed surgical space, these devices present several different problems. One problem is that the bags are collapsible so that a considerable amount of manipulation is required by the limited quantity of tools so as to hold the mouth of the bag open and steady so that the loose tissue can be brought to the opening before it is stuffed within the bag. Two or more graspers may be required just to hold the bag open also requiring a third grasper to bring the sample tissue to the open end of the bag.

Once the opened prior art bag is held steady a further grasper must be used to grab the tissue, stuff it into the bag, release the tissue and withdraw the grasper, grab the tissue at a new location stuff that portion into the bag, release the tissue and repeat the operation until the tissue is loaded within the bag completely. This operation requires extensive tool manipulation and is very time consuming. As the bag is loaded from the open end, gas may be trapped inside the bag as the bag collapses around the soft, wet tissue. This captured gas may result in stiffening of the bag so that further loading of the bag becomes difficult or impossible. Although the bag's gas pressure is slight while it is in the pressurized body cavity, once the bag is brought out to atmospheric pressure the captured gas tries to escape from the bag. This may cause expulsion of the bag's contents, contaminating the sterile field and possibly splattering the surgical team with bodily fluids.

Further more specific arrangements of the prior art are shown for example in the following U.S patents such as U.S. Pat. No. 5,176,687 to Hasson et al with a disposable pouch utilizing a rather complicated mechanism to reach within the body cavity to retrieve a tissue therein. A further device is shown in U.S. Pat. No. 5,190,561 to Graber showing a cone shaped bag with an open end thereon. U.S. Pat. No. 5,643,282 to Kieturakis shows an expandable wire cage which surrounds the tissue being sought. U.S. Pat. No. 5,779,716 to Cano et al shows a loose bag on the end of a wire rim for capturing a tissue sample. U.S. Pat. No. 5,853,374 to Hart et al shows an enclosure on the distal end of a shaft of a flat thereon to scoop and contain a tissue therewithin. This prior art shows a rather complicated and somewhat ineffective means for retrieving a body tissue from a body cavity. These devices fail to readily enclose the tissue and prevent it from being captured in a fully enclosed, safe, efficient and convenient manner.

It is the object of the present invention to overcome the disadvantages of the prior art.

It is a further object of the present invention to provide a tissue retrieval arrangement which will envelop the tissue and enclose it as it is being withdrawn from the body cavity.

It is a further object of the present invention, to provide a tissue retrieval arrangement which will minimize or eliminate the leakage of tissue from the retrieval device.

BRIEF SUMMARY OF THE INVENTION

The present invention relates to an organ or tissue retrieval bag arrangement utilizable in a laparoscopic surgical procedure. The organ retrieval bag in its preferred embodiment, comprises a generally cylindrically shaped, flexible, thin walled member having a first or proximal end and a second or distal end. The material of the retrieval bag may be made for example, from a latex or a plastic material. The first end is preferably open, and the second end or distal end is preferably closed in this first embodiment.

The distal end of the bag may be tapered to a narrower diameter than the diameter of the proximal end of the bag to facilitate eversion of that bag about a tissue sample, as will be explained hereinbelow.

The distal end has a pair of generally tapered tubular-shaped grasper receiving tips extending thereon. The grasper receiving tips are preferably unitary with the wall portions of the retrieval bag. The grasper receiving tips are spaced apart from one another each preferably having a flattened opposed wall facing its adjacent receiving tip. The grasper receiving tips are spaced apart so as to permit a portion of a tissue being retrieved to be received and engaged therebetween. The first or proximal end of the retrieval bag may have an annular band therearound to permit grasping of that end of the retrieval bag and to provide a strengthened end thereat.

A plurality of generally axially arranged ribs, pleats or folds may be molded into the sidewall of the retrieval bag in a spaced apart manner to provide additional volume or expansion for larger tissue sample retrieval A grasper such as an Endopath(tm) grasper for example, is inserted inside the elongated organ retrieval bag. The grasper device has a handle on a proximal end thereof and a pair of grasper jaws on its distalmost end thereof. Movement of the handle effects opening and closing of the elongated grasper jaws in a manner known in the art.

Before a surgical procedure utilizing the present invention, the elongated grasper device is inserted within the organ retrieval bag, so that the grasper jaws are disposed and mate within the respective grasper receiving tips of the organ retrieval bag. The organ retrieval bag is then inserted through a pre-placed trocar which has been inserted through a surgical incision within the patient (i.e. abdomen). Once an organ or tissue has been properly excised by other surgical instruments, and the surgeon has located the tissue with a video image of the internal organs, the distalmost end of the organ retrieval bag with its opposed grasper receiving tips may be directed toward that tissue to be retrieved. The tissue is then at least partially seized between the grasper receiving tips as the handle of the grasper device is actuated so as to effect the pinching together of the opposed grasper jaws. A second grasper device should be manipulated within the peritoneum of the patient and grab the beading at the proximal end of the organ retrieval bag and pull it distally, so as to evert the organ retrieval bag and pull it off of the grasper device beginning at the proximal end thereof and thence over and about the organ/tissue being grasped by the grasper jaws therein.

Thus the original inner side of the organ retrieval bag thus becomes the outer side when it has been utilized to surround the tissue being retrieved. The original outer side of the organ retrieval bag thus becomes the inner side of the tissue containment bag once it has been pulled distally from the grasper device and about the tissue/organ being retrieved. The tissue then may be safely enveloped within the everted organ retrieval bag and removed through the trocar or surgical opening in the patient, without loss of any contaminated fluid or without contaminating tissue components escaping therefrom.

The organ retrieval bag in a further embodiment, may have a closure arrangement on its proximalmost end such as a draw string or a closure cord extending through a loop or ring, so as to be tightenable by the surgeon after the retrieval bag has been everted and made to surround and envelop the tissue being retrieved.

In a further embodiment of the organ retrieval bag, the second or distalmost end may have an opening thereat, about which the grasper jaws are disposed. The grasper jaws may be received in grasper receiving tip or alternatively in a further preferred embodiment, the grasper jaws may extend distally of the distal end of the organ retrieval bag so as to directly enable the tissue to be grabbed directly and retrieved thereby.

In yet a further preferred embodiment of the present invention, the distal tip of the retrieval bag may be comprised of three or more receiving tips for the jaws of a grasper therewithin. Each receiving tip being separated from its adjacent tip by a slot arranged therebetween, and each receiving tip containing a grasper jaw from a multi-jawed grasper device.

Thus what has been shown is a unique arrangement for retrieving tissue parts, body organs or samples of a excised body component while minimizing or eliminating any danger from contaminating adjacent body parts or injuring the patient thereby.

The invention thus comprises a tissue retrieval arrangement for enclosably retrieving body tissue from a mammalian body cavity comprising: an elongated thin walled sheath-like retrieval bag having a proximal end and a distal end; an arrangement of receiving tips on the distal end of the sheath to permit receipt of a grasper jaw in each of the receiving tips and thus permit safe retrieval of a body tissue between the receiving tips moved by the grasper jaws therewithin. The retrieval bag is evertable. The proximal end of the retrieval bag has tightenable closure arrangement thereon. The proximal end of the retrieval bag may have a bead extending therearound. The retrieval bag may have an arrangement of expandable folds or pleats generally axially arranged near a mid portion thereof to permit volumetric expansion of the bag if necessary for a large tissue sample being retrieved. The tightenable closure arrangement may comprise a loop and draw cord arranged therearound. The distal end of the retrieval bag may be closed. The distal end of the retrieval bag may have an opening therethrough. The receiving tips may have a thickened inner surface to facilitate secure receipt of the grasper jaws therewithin. Each of the receiving tips defines a slot with an adjacent receiving tip, to provide a channel for entry of a body tissue therein.

The invention also may comprise a method of retrieving body tissue from a body cavity of a mammalian patient comprising the steps of: placing an elongated grasper device with a jaw arranged on a distal end thereof into an elongated tissue retrieval bag having a proximal end and a distal end, the retrieval bag having receiving tips on the distal end thereof to receive the jaws respectively therein; severing a tissue from a body portion of the patient; grasping the tissue by manipulating the jaws and the receiving tips onto the tissue; everting the retrieval bag about the tissue; and withdrawing the retrieval bag with the tissue now inside, from the body cavity of the patient. The method of retrieving body tissue may also include: pulling the proximal end of the retrieval bag in a distal direction over itself to effect the everting thereof with the body tissue now on the inside thereof; tightening a closure arrangement on the distal end of the retrieval bag to prevent loss of any tissue therefrom; arranging an opening on the distal end of the retrieval bag to permit each of the jaws to extend through the opening so that the jaws may directly grasp the tissue; thickening the receiving tips to permit the jaws to be securably received therein; placing at least three receiving tips in the distal end of the receiving bag for receipt of a jaw therein.

The invention may also include a method of retrieving body tissue from a body cavity of a mammalian patient comprising the steps of placing an elongated grasper device with a jaw arranged on a distal end thereof into an elongated tissue retrieval bag having a proximal end and a distal end, the retrieval bag having receiving tips on the distal end thereof to receive the jaws respectively therein; severing a tissue from a body portion of the patient; grasping the tissue by manipulating the jaws and the receiving tips onto the tissue; pulling on the proximal end of the retrieval bag to evert the bag about the tissue being grasped; and withdrawing the retrieval bag with the tissue now in the everted bag, from the body cavity of the patient.

BRIEF DESCRIPTION OF THE DRAWINGS

The objects and advantages of the present invention will become more apparent when viewed in conjunction with the following drawings in which.

DETAILED DESCRIPTION OF THE PREFERRED EMBODIMENTS

Figure 1:
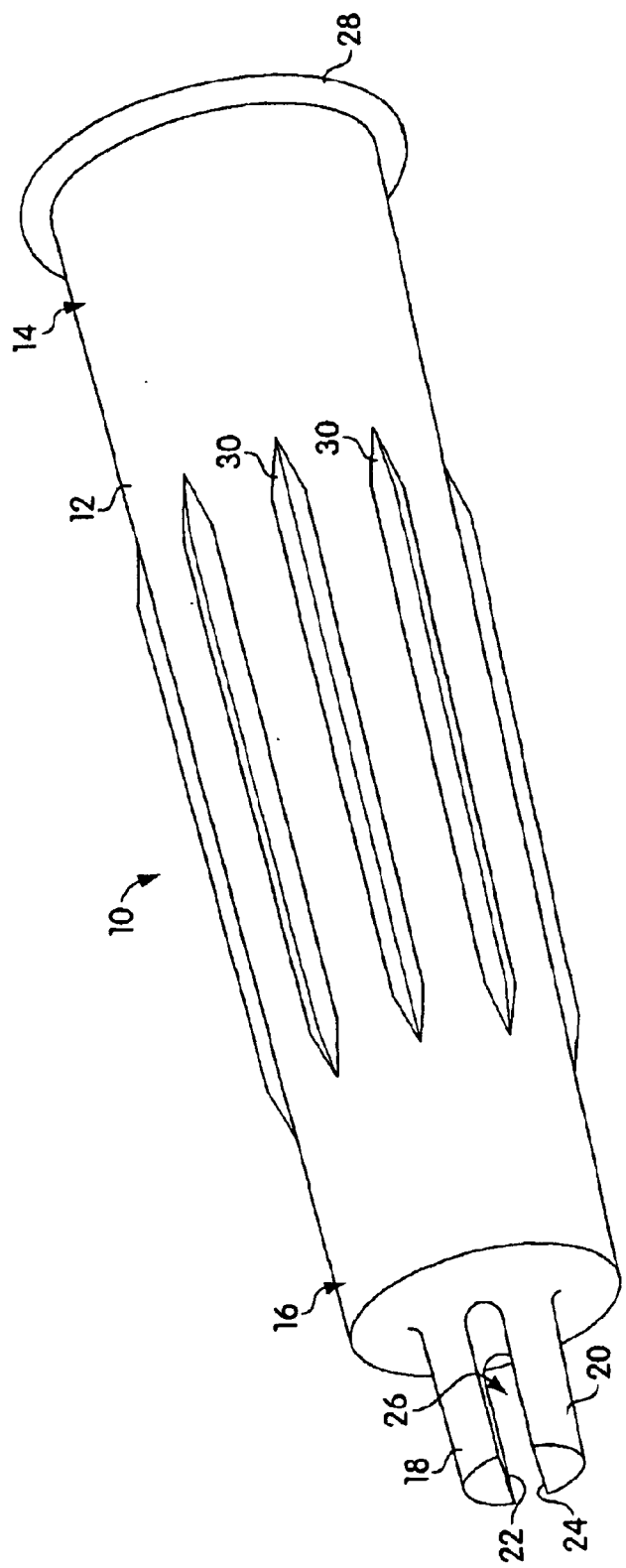
FIG. 1 is a perspective view of a tissue or organ retrieval bag.

Referring now to the drawings in detail, and particularly to FIG. 1, there is shown the present invention which comprises an organ or tissue retrieval bag arrangement 10 particularly utilizable in a laparoscopic surgical procedure. The organ retrieval bag arrangement 10 in its preferred embodiment, comprises a generally cylindrically shaped, flexible, thin walled member or bag 12 having a first or proximal end 14 and a second or distal end 16. The material of the retrieval bag 12 may be made for example, from a latex or a plastic material. The first end 14 is preferably open, and the second end or distal end 16 is preferably closed in this first embodiment.

The distal end 16 may be tapered to a narrower diameter than the diameter of the proximal end 14 to facilitate eversion of the bag 12, as will be described hereinbelow.

Figure 7:
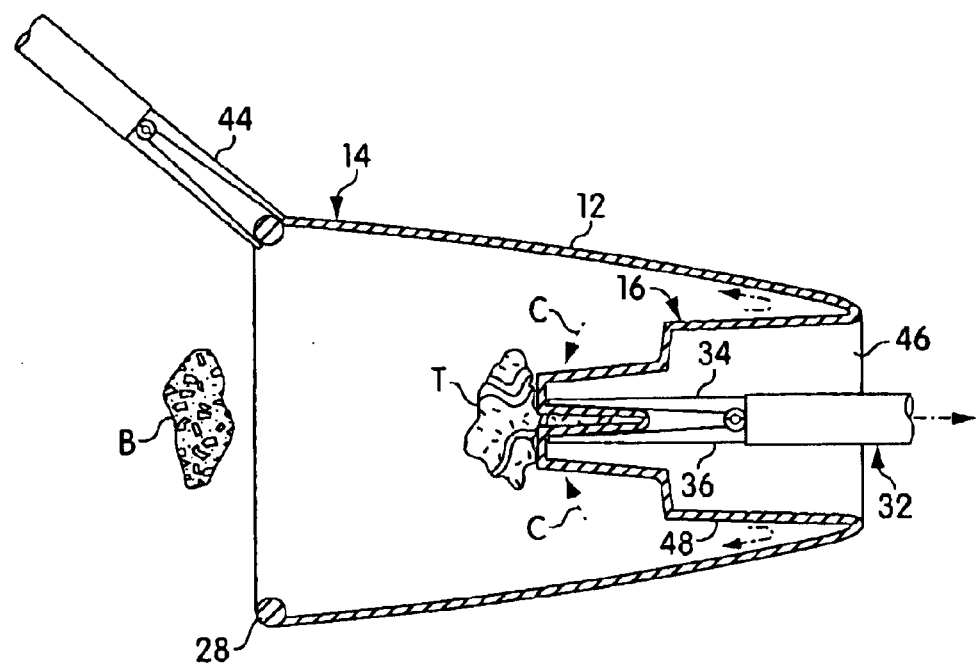
FIG. 7 is a side elevational view of an organ retrieval bag being everted about a tissue sample.

The distal end 16 of the retrieval bag 12 has a pair of generally tapered tubular-shaped grasper receiving tips 18 and 20 extending thereon. The wall surface of the grasper receiving tips 18 and 20 are preferably unitary with the wall portions of the retrieval bag 12. The grasper receiving tips 18 and 20 are spaced apart from one another each preferably having a flattened opposed wall 22 and 24 facing its adjacent receiving tip 20 and 18, as may be seen in FIGS. 1 and 2. The grasper receiving tips 18 and 20 are spaced apart to define a channel 26 therebetween, as shown in FIGS. 1 and 2, and thus to permit a portion of an organ or tissue "T" being retrieved to be received and engaged therebetween, as represented in FIGS. 2 and 7.

Figure 2:
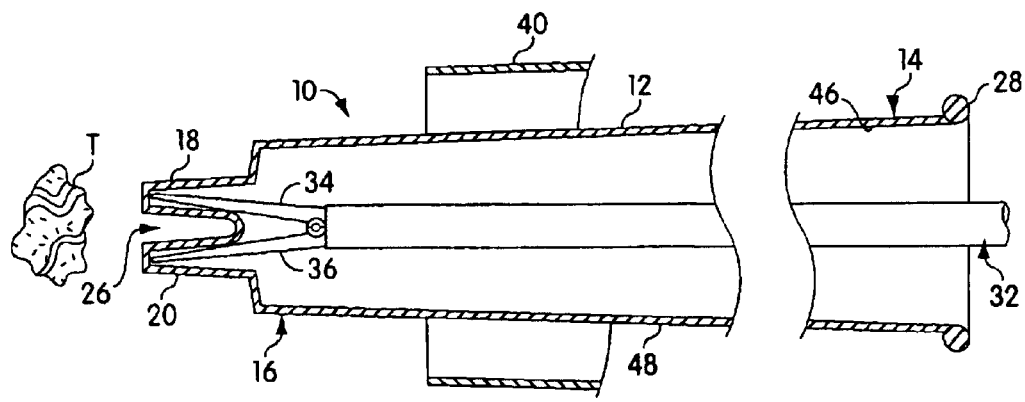
FIG. 2 is a side elevational view of an organ or tissue retrieval bag showing a grasper arranged therewithin.

The first or proximal end 14 of the retrieval bag 12 may have an annular band 28 therearound, as shown in FIGS. 1 and 2, to permit grasping of that end of the retrieval bag 12 and to provide a strengthened end thereat, for retrieval purposes as will be described hereinbelow.

A plurality of generally axially disposed folds or pleats 30 may be molded into the sidewall of the retrieval bag 12 in a spaced apart manner as shown in FIG. 1, to provide for expansion of the bag 12 when necessary during retrieval of a relatively large tissue sample.

An elongated tissue grasper 32, such as an Endopath(tm) grasper for example, as depicted in FIGS. 2, 5, 5A and 7, is inserted inside the elongated organ retrieval bag 12. The grasper device 32 has a handle on a proximal end thereof (not shown for clarity of the drawings), and a pair of grasper jaws 34 and 36 on its distalmost end thereof. Movement of the handle typically effects opening and closing of the elongated grasper jaws 34 and 36 of a grasper in a manner known in the art.

Figure 5:
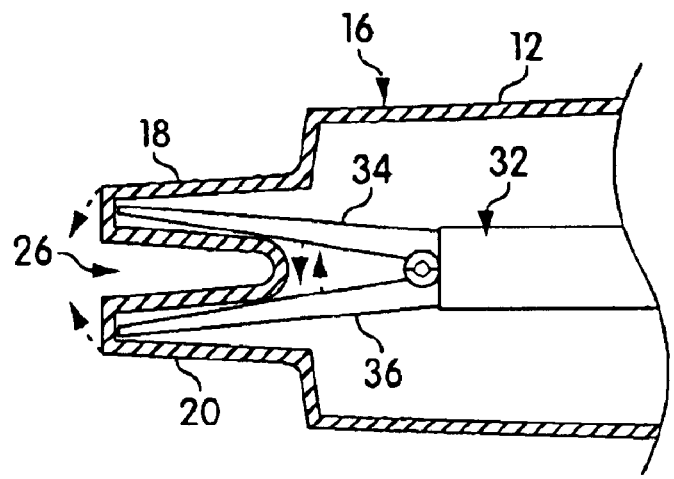
FIG. 5 is an enlarged side elevational view of the organ retrieval bag.

Before proceeding with a surgical procedure utilizing the present invention, the elongated grasper device 32 is inserted within the organ retrieval bag 12, so that the grasper jaws 34 and 36 are disposed and mate within the respective grasper receiving tips 18 and 20 of the organ retrieval bag 12 as may be seen in FIGS. 2, 5 and 7. The organ retrieval bag 12 is then inserted through a pre-placed trocar 40, as depicted in FIG. 2, which trocar 40 has been inserted through a surgical incision within the patient (i.e. abdomen).

Once an organ or tissue "T" has been properly excised by other surgical instruments and the surgeon has located the tissue "T" with a video image of the internal organs, the distalmost end 16 of the organ retrieval bag 12 with its opposed grasper receiving tips 18 and 20 may be directed toward that tissue "T" to be retrieved. The tissue "T" is then at least partially seized between the grasper receiving tips 18 and 20 as the handle of the grasper device 32 is actuated so as to effect the pinching together of the opposed grasper jaws 34 and 36, as depicted by arrows "C" in FIG. 7. A second grasper device 44 would preferably be manipulated within the peritoneum of the patient and grab the beading 28 at the proximal end 14 of the organ retrieval bag 12 (after the proximal end 14 of the retrieval bag 12 has been pushed clear of the distal end of the trocar 40) and pull the retrieval bag 12 in a distal direction about the severed and excised tissue "T" from its body portion "B", so as to evert the organ retrieval bag 12 and pull it off of the tissue grabbing grasper device 32, as depicted in FIG. 7, the everting beginning at the proximal end 14 thereof and thence over and about the organ/tissue "T" being grasped by the grasper jaws 34 and 36 therein.

Thus the original inner side 46 of the organ retrieval bag 12 thus becomes the outer side when it has been utilized to surround the tissue "T" being retrieved. The original outer side 48 of the organ retrieval bag 12 thus becomes the inner side of the tissue containment bag once it has been pulled distally from the grasper device 32 and about the tissue/organ "T" being retrieved, as exemplified in FIG. 7. The tissue "T" then may be safely enveloped within the everted organ retrieval bag 12 and removed through the trocar 40 or surgical opening in the patient, without loss of any contaminated fluid or without contaminating tissue components escaping therefrom.

Figure 3:
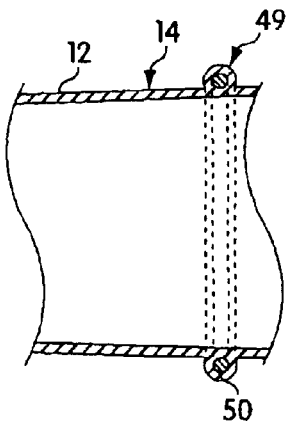
FIG. 3 is a side elevational view of a further embodiment of the proximal end of the organ retrieval bag shown in FIG. 2.
Figure 4:
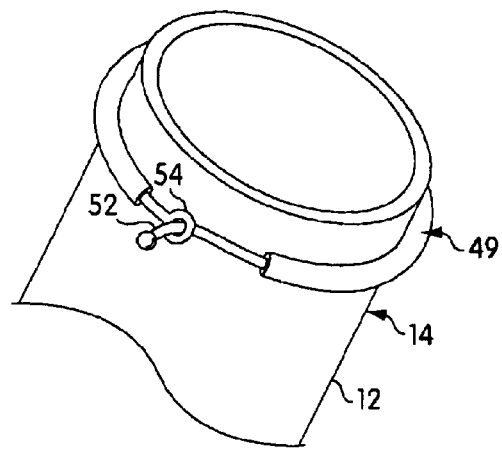
FIG. 4 is a perspective view of a further closure arrangement of the proximal end of the organ retrieval bag shown in FIG. 2.

The organ retrieval bag 12 in a further embodiment as represented in FIGS. 3 and 4, may have a closure arrangement 49 on its proximalmost end 14 such as an elasticized closure cord 50 or a draw string 52 extending through a loop or ring 54, so as to be tightenable by the surgeon after the retrieval bag 12 has been everted and made to surround and envelop the organ/tissue "T" being retrieved.

FIG. 5 shows an enlarged side elevational view of the apparatus shown in FIG. 2 with the jaws 34 and 36 within tips 18 and 20 of the bag 12.

Figure 5A:
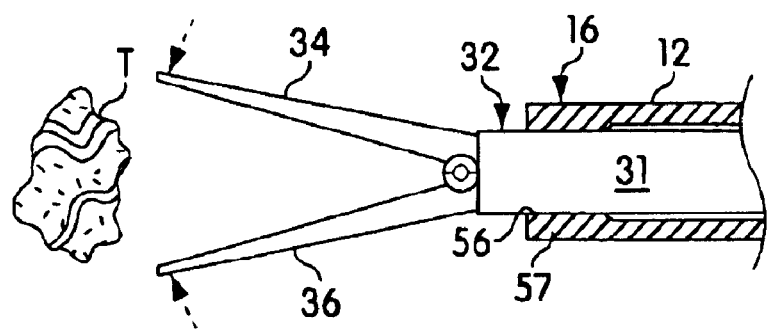
FIG. 5A is a further embodiment of the organ retrieval bag shown in FIG. 5.

In a further embodiment of the organ retrieval bag 12, as shown in FIG. 5A, the second or distalmost end 16 may have an opening 56 thereat, with a thickened annular lip 57 to provide a fluid tight seal with the distal end of the shaft 31 of the grasper 32 and through which the grasper jaws 34 and 36 may extend distally beyond the distal end 16 of the organ retrieval bag 12 so as to themselves directly enable the tissue "T" to be grabbed directly and retrieved by the jaws 34 and 36 themselves, then to be "swallowed" by an everted bag 12.

Figure 6:
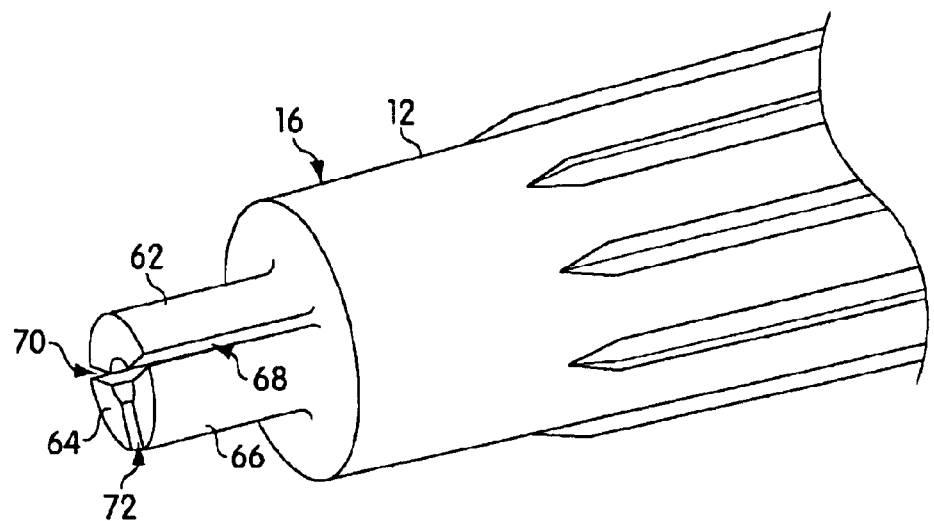
FIG. 6 is a further embodiment of an organ tissue retrieval bag having a multiple receiving tips thereon.

In yet another further preferred embodiment of the present invention as shown in FIG. 6, the distal tip 16 of the retrieval bag 12 may be comprised of three or more receiving tips 62, 64 and 66 for the jaws of a grasper therewithin (not shown). Each receiving tip 62, 64 and 66 being separated from its adjacent tip by a slot 68, 70 and 72 arranged between adjacent receiving tips 62, 64 and 66, each receiving tip 62, 64 and 66 containing a grasper jaw (not shown) from a multi-jawed grasper device (also not shown).

Thus what has been shown is a unique arrangement for retrieving tissue parts, body organs or samples of a excised body component while minimizing or eliminating any danger from contaminating adjacent body parts or injuring the patient thereby.

I claim:

1. A method of retrieving body tissue from a body cavity of a mammalian patient comprising:

placing an elongated grasper device with jaws arranged on a distal end thereof into an elongated tissue retrieval bag having a proximal end and a distal end, said retrieval bag having receiving tips on said distal end thereof to receive said jaws respectively therein;

severing a tissue from a body portion of the patient;

grasping said tissue by manipulating said jaws and said receiving tips onto said tissue;

everting said retrieval bag about said tissue; and withdrawing said retrieval bag with said tissue now inside, from said body cavity of the patient.

2. The method of retrieving body tissue as recited in claim 1, including:

pulling said proximal end of said retrieval bag in a distal direction over itself to effect the everting thereof with the body tissue now on the inside thereof.

3. The method of retrieving body tissue as recited in claim 1, including:

tightening a closure arrangement on said distal end of said retrieval bag to prevent loss of any tissue therefrom.

4. The method of retrieving body tissue as recited in claim 1, including:

arranging an opening on said distal end of said retrieval bag to permit each of said jaws to extend through said opening so that said jaws may directly grasp said tissue.

5. The method of retrieving body tissue as recited in claim 1, including:

inserting said jaws in said receiving tips to permit said bag to grasp a tissue thereby.

6. The method of retrieving body tissue as recited in claim 1, including:

placing at least three receiving tips in said distal end of said receiving bag for receipt of said jaws therein.

7. A method of retrieving body tissue from a body cavity of a mammalian patient comprising:

placing an elongated grasper device with jaws arranged on a distal end thereof into an elongated tissue retrieval bag having a proximal end and a distal end, said retrieval bag having receiving tips on said distal end thereof to receive said jaws respectively therein as said grasper is inserted into said bag;

severing a tissue from a body portion of the patient;

grasping said tissue by manipulating said jaws and said receiving tips onto said tissue;

pulling on said proximal end of said retrieval bag to evert said bag about said tissue being grasped; and withdrawing said retrieval bag with said tissue now in said everted bag, from said body cavity of the patient.

* * * * *